United States Patent
Riggs

(10) Patent No.: US 6,302,900 B1
(45) Date of Patent: Oct. 16, 2001

(54) HOLISTIC METHOD OF TREATING INJURED OR PATHOLOGIC TISSUE WITH A LASER

(76) Inventor: Jeffrey M. Riggs, 2375 Vantage Dr., Colorado Springs, CO (US) 80919

(*) Notice: Subject to any disclaimer, the term of this patent is extended or adjusted under 35 U.S.C. 154(b) by 0 days.

(21) Appl. No.: 09/525,675

(22) Filed: Mar. 15, 2000

(51) Int. Cl.[7] .................................................. A61N 5/006
(52) U.S. Cl. ........................ 607/89; 600/548; 607/88; 607/92; 128/898
(58) Field of Search ............................ 600/548; 128/907, 128/898; 606/3, 9, 27, 32–35, 44; 607/88, 89, 92

(56) References Cited

U.S. PATENT DOCUMENTS

| | | | |
|---|---|---|---|
| 4,535,784 | * 8/1985 | Rohlicek et al. | 128/735 |
| 5,133,352 | * 7/1992 | Lathrop et al. | 128/419 |
| 5,713,375 | * 2/1998 | McAllister | 128/898 |
| 5,843,074 | * 12/1998 | Cocilovo | 606/10 |
| 5,945,119 | * 8/1999 | Lai | 424/443 |
| 6,074,411 | * 6/2000 | Lai et al. | 607/89 |

* cited by examiner

*Primary Examiner*—John Mulcahy
*Assistant Examiner*—Ahmed Farah
(74) *Attorney, Agent, or Firm*—G. F. Gallinger

(57) ABSTRACT

A holistic method of therapeutic laser treatment for body tissues in a problematic area, comprising the following steps: using a laser discharge probe to irradiate the tissues in the problematic area and additionally treating a body energy path through the problematic area by irradiating the body tissues along an energy path, as defined in Eastern medicine, through the problematic area so that energy flow is normalized in the problematic area. One aspect of this provides for a method as above wherein the energy flow path comprises meridians of energy flow as defined in acupuncture and wherein treatment points along the energy flow path comprise acupuncture points. In yet another preferred aspect, the energy flow path comprises Jin Shin Jyutsu energy flow paths and the treatment points along the energy flow paths comprise energy spheres. Stimulating tissue along an energy path in the body rectifies energy flow through the specific body area and thereby alleviate problems in that area of concern.

19 Claims, 2 Drawing Sheets

HOLISTIC METHOD OF TREATING INJURED OR PATHOLOGIC TISSUE WITH A LASER

FIELD OF THE INVENTION

This invention relates to the treatment of injured or pathologic tissue in the body with a laser. More particularly this invention relates to a holistic method of treating the tissue wherein not only the injured or pathologic tissue is stimulated; but additionally, tissues along related body energy paths, as defined and recognized in Eastern medicine, are stimulated with the laser. The laser stimulation normalizes natural body energy flow and facilitates normal cellular activity in pathological areas.

BACKGROUND OF THE INVENTION

The warming and therapeutic effect of laser light on body tissue is known. U.S. Pat. No. 5,445,146 issued to G. J. Bellinger in 1995 discloses the use of a laser to reduce pain, to reduce inflammation, and to enhance healing.

The applicants have intimate familiarity with acupuncture as well as laser therapy of body tissues. In Eastern Medicine body energy paths are defined as meridian pathways and Jin Shin Jyutsu energy pathways. In acupuncture a localized tissue problem area is treated by needling trigger points consisting of nerve endings known to be interconnected along an energy flow path to the localized problem area.

In their practice the applicants have worked with individuals having problems generally perceived as being specific to a local body area as well as individuals having more systemic nerve diseases. Following protocols of laser treatments along body energy paths, where acupuncture points of nerve endings were targeted, remarkable recoveries from chronic pains and even reversals in incurrable diseases have been achieved.

OBJECTS OF THE INVENTION

It is an object of this invention to disclose a method of stimulating injured or pathologic tissue with a laser. It is an object of this invention to disclose a method of treating a problem identified with a specific body area by stimulating tissue along an energy path in the body to rectify energy flow through the specific body area and thereby alleviate problems in that area of concern. It is yet a further object of this invention to disclose a holistic method of treating the body with laser therapy; a method which has resulted in remarkable recoveries from chronic pains and even reversals in the progression of diseases generally considered to be irreversible.

One aspect of this invention provides for a holistic method of therapeutic laser treatment for body tissues in a problematic area, comprising the following steps: using a laser discharge probe to irradiate the tissues in the problematic area and additionally treating a body energy path through the problematic area by irradiating the body tissues along an energy path, as defined in Eastern medicine, through the problematic area so that energy flow is normalized in the problematic area.

Another aspect of this provides for a method as above wherein the energy flow path comprises meridians of energy flow as defined in acupuncture and wherein treatment points along the energy flow path comprise acupuncture points. In yet another preferred aspect of this invention the energy flow path comprises Jin Shin Jyutsu energy flow paths and the treatment points along the energy flow paths comprise energy spheres.

Various other objects, advantages and features of this invention will become apparent to those skilled in the art from the following description in conjunction with the accompanying drawings.

FIGURES OF THE INVENTION

Figure 2:
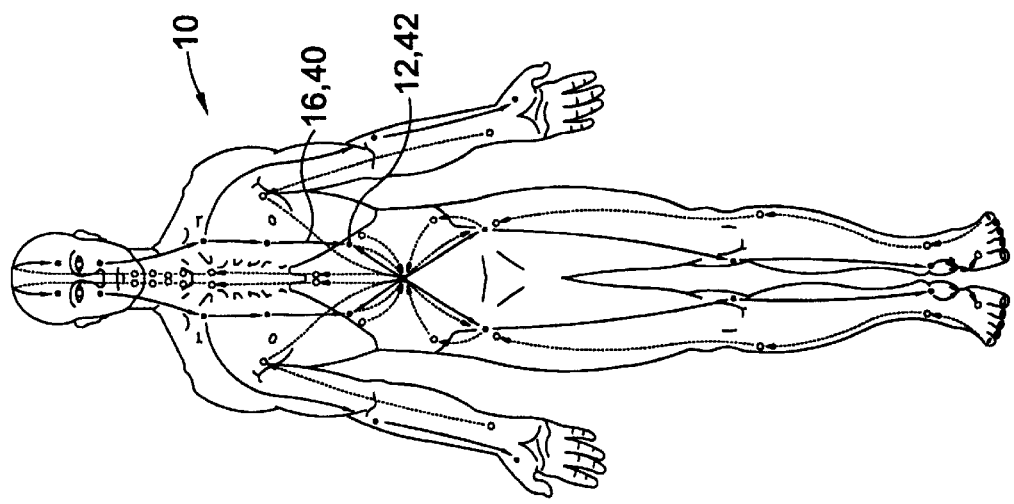
FIG. 2 is a schematic view of a body having energy flow paths as defined in Jin Shin Jyutsu and major treatment points therealong which comprise energy spheres. Posterior treatment points and energy flow paths are connected by broken lines; anterior treatment points and energy flow paths are connected by solid lines.

The following is a discussion and description of the preferred specific embodiments of this invention, such being made with reference to the drawings, wherein the same reference numerals are used to indicate the same or similar parts and/or structure. It should be noted that such discussion and description is not meant to unduly limit the scope of the invention.

DESCRIPTION OF THE INVENTION

Figure 1:
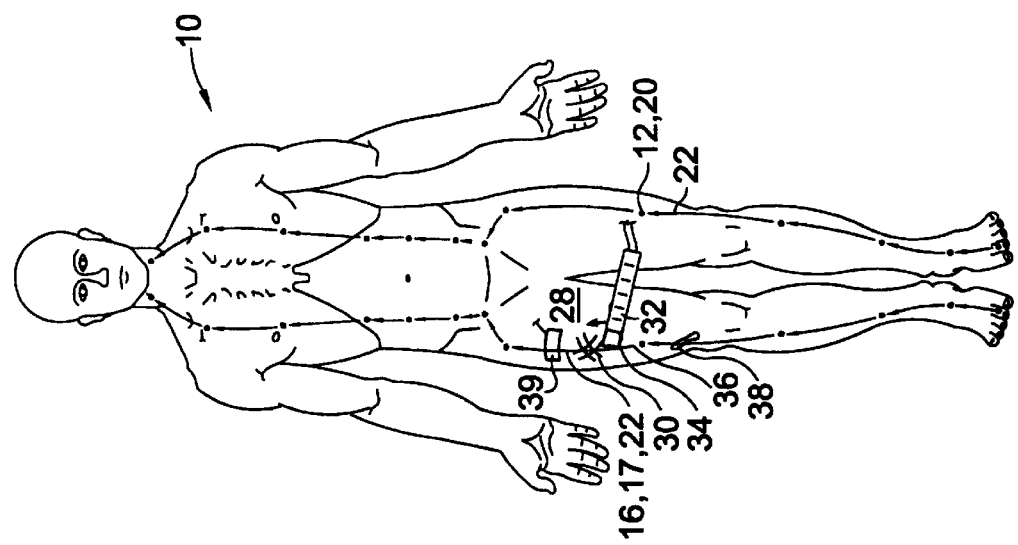
FIG. 1 is a schematic view of a body having major treatment points which comprise acupuncture points along the meridians of energy flow marked thereon.

Turning now to the drawings and more particularly to FIG. 1 we have a schematic view of a body 10 having major treatment points 12 along paths 14 of energy flow 16. A general holistic method of therapeutic laser treatment for body tissues 28 in a problematic area 30 comprises the following steps: using a laser discharge probe 32 to irradiate the tissues 28 in a problematic area 30 and then, additionally treating a body energy path 16 through the problematic area 30 by irradiating the body tissues 28 along the energy path 16 through the problematic area 30 so that energy flow 17 is normalized in the problematic area 30.

In this invention energy flow 17, energy flow paths 16, and treatment points 12 are generally used as defined in Eastern medicine. A preferred aspect of this invention further comprises the step of additionally treating neurological malfunctioning sensory and motor nerve sites 34.

More particularly, FIG. 1 shows the Eastern acupuncture school of philosophy and practice wherein the treatment points 12 are acupuncture points 20; and wherein the paths of energy flow paths 16 are called meridians 22. A preferred aspect of the general holistic method of therapeutic treatment of this invention is described by the general holistic method of therapeutic treatment above wherein an energy flow path 16 comprises a meridian of energy flow 22 as defined in acupuncture; and wherein the treatment points 12 along the meridians of energy flow 22 comprise acupuncture points 20. Another preferred aspect of this invention, further comprises the step of additionally treating sites 36 along the meridians 22 of energy flow 17 which comprise less dense concentrations of nerve endings than acupuncture points 20.

FIG. 2 is a schematic view of a body 10 having energy flow paths 16 which are Jin Shin Jyutsu energy flow paths 40, and major treatment points 12 which comprise Jin Shin Jyutsu treatment points, Jin Shin Jyutsu, like acupuncture, is a leading Eastern school of philosophy and practice. The Jin Shin Jyutsu treatment points 42 comprise energy spheres. On FIG. 2 posterior Jin Shin Jyutsu energy flow paths 40 and posterior Jin Shin Jyutsu treatment points 42 are connected by broken lines, whereas anterior Jin Shin Jyutsu energy flow paths 40 and Jin Shin Jyutsu treatment points 42 are connected by solid lines. A preferred aspect of the general holistic method of therapeutic treatment of this invention is described above by the general holistic method of therapeutic treatment above wherein the energy flow path 16 comprises a Jin Shin Jyutsu energy flow path 40 and wherein the treatment points 12 along the Jin Shin Jyutsu energy flow paths 40 comprise Jin Shin Jyutsu treatment points 42 which are energy spheres.

In all of the aspects of the general method of therapeutic treatment described above most preferably the treatment is along the energy flow path 16,22,40 in a direction of energy flow 17 as defined in Eastern medicine. (This direction is shown on the drawings.) And generally, vestiges of former injury 38 (scar tissues) are targeted to promote healing and reduce inherent impedance to energy flow therethrough. In all aspects of the general method of therapeutic treatment described above the methods may include the additional step of further evaluating effected changes with Kirlian photography to ensure energy flow 17 has been normalized. And in all aspects of the general method of the general holistic therapeutic treatment described above the method may include the additional step of dragging the laser discharge probe 32 along the energy path 16 to facilitate normalization of energy flow 17 therealong. Similarly the methods may include the additional step—of using a grounded metal plate 39, positioned along the energy path 16 to facilitate conduction of the energy flow 17 thereto.

Figure 3:
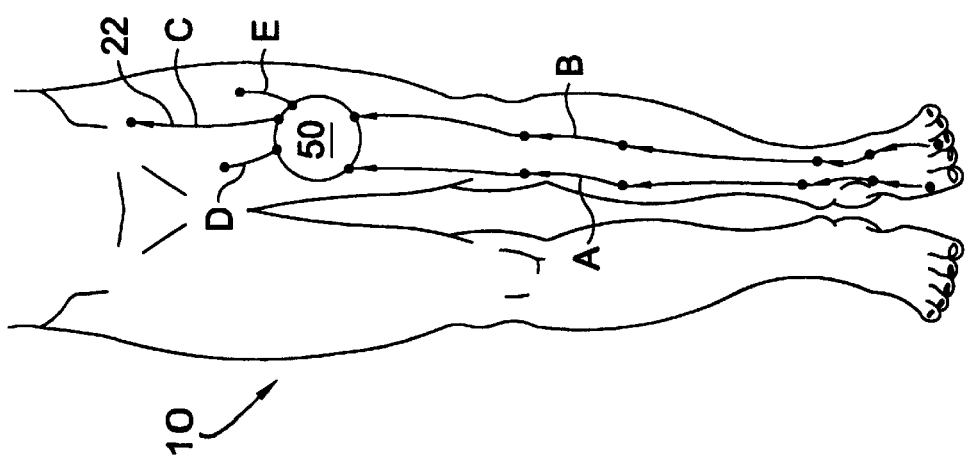
FIG. 3 is a schematic drawing showing a method of treating a diabetic neuropathies.

FIG. 3 is a schematic drawing showing a method of treating a diabetic neuropathy 50. In this drawing a method of treating a neuropathy 50 on the left thigh is shown. The laser discharge probe 32 is first dragged upwardly along Jin Shin Jyutsu energy flow path A. Jin Shin Jyutsu treatment points 42 shown on path A are irradiated as the laser discharge probe 32 is dragged therealong. Additionally less dense concentrations of nerve endings therebetween are irradiated. Similarly the laser discharge probe is dragged upwardly in the direction of energy flow along path B and C. Next the laser discharge probe 32 is dragged downwardly along motor nerve path D, and then finally the laser discharge probe 32 is dragged downwardly along sensory nerve path E.

Figure 4:
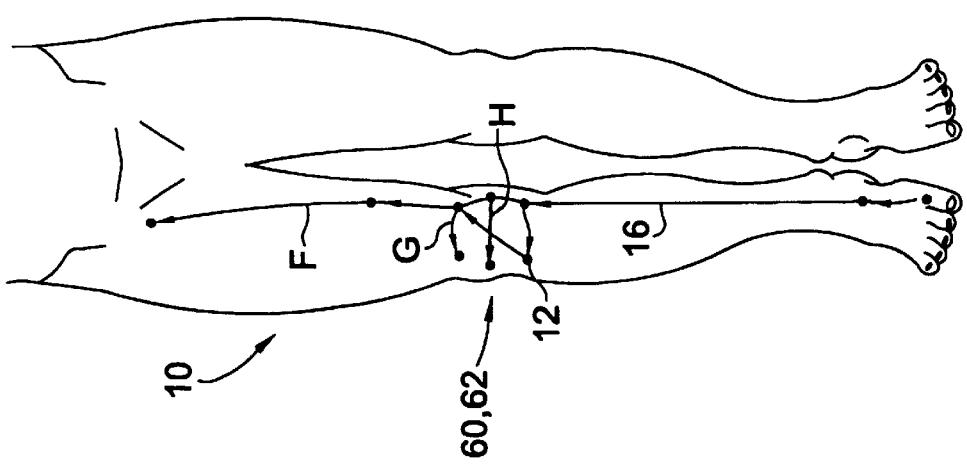
FIG. 4 is a schematic drawing showing a method of treating a knee injury.

FIG. 4 is a schematic drawing showing a method of treating a joint 60 injury. More particularly FIG. 4 shows the method of treating a knee 62 injury. The laser discharge probe 62 is dragged upwardly along energy path F through the problematic area, the knee 62, irradiating the treatment points 12, the lesser concentrations of nerve endings therebetween along the energy path 16, all in the direction of energy flow 17. Finally the laser discharge probe is dragged between the treatment points 12 along energy paths G and H on the knee 62 itself as shown.

Figure 5:
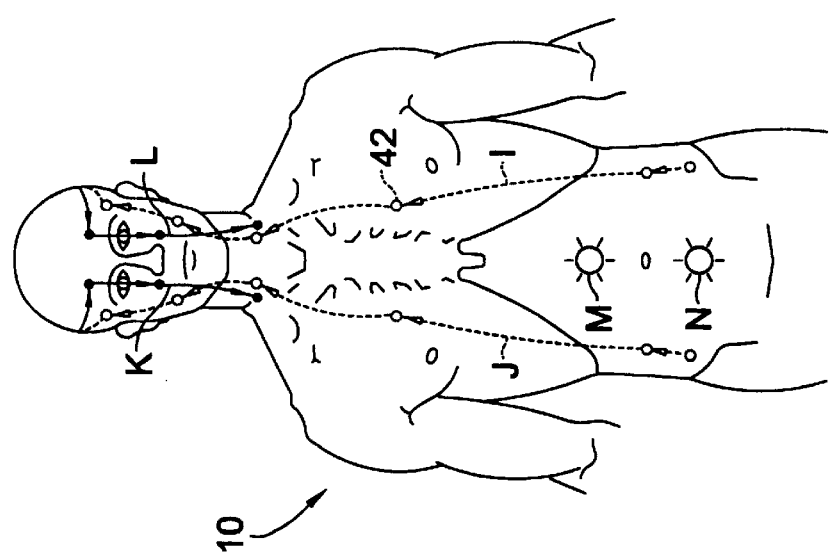
FIG. 5 is a schematic drawing showing a method of treating a migraine headache.

FIG. 5 is a schematic drawing showing a method of treating pain in a particular problematic body area. More particularly FIG. 5 shows a method of treatment for a migraine headache. The laser discharge probe 32 is first dragged upwardly along acupuncture energy flow paths I and J. Energy flow paths I and J, on the posterior side of the body 10 are shown with broken lines. Acupuncture treatment points 42 shown on path I and J are irradiated as the laser discharge probe 32 is dragged therealong. Additionally less dense concentrations of nerve endings therebetween are irradiated. Similarly the laser discharge probe is dragged downwardly in the direction of energy flow along Jin Shin Jyutsu energy flow paths K and L on the anterior side of the body as shown on energy flow paths K and L. Finally chakras M and N are irradiated so that energy flow therein and around is normalized. Chakras M,N as defined in Eastern medicine are centers of energy in the body 10.

In some applications (not shown) adjacent energy paths 16 are irradiated to eliminate crossover to the energy path through the problematic area 30 to reestablish normal energy flow 17 thereby.

In the above methods the total energy / area applied to each individual site is generally in the range of 18–240 joules/ cm.cm. This energy is sufficient energy to produce tissue warming, but insufficient energy to thermally damage the tissue. The irradiance rate at the treatment site is in the range of generally 100–1200 mw/ cm.cm. The areas of the treatment sites range between 0.1 to 5 cm.cm. The laser wavelength is generally in the range of 400–1400 nanometres; most preferably the wavelength is 915 nanometres. The laser irradiance may be either pulsed or continuous. The treatment may include a plurality energy densities and wavelengths.

The method of laser irradiation along an energy path 16 through a problematic area 30 on the body 10 is based on an understanding of the natural body energy flow paths 16 and clinical results observed when applying treatment protocols developed through refined study and observation. Pathological and injured tissue causes an impediment to body energy flow 17 and creates increased electrical resistance that can be scientifically measured. The method of laser irradiation along an energy path 16 in the direction of energy flow 17 through a problematic area 30 on the body 10 re-establishes natural body energy flow 17. In practice the applicants have worked with individuals having systemic and immune system related diseases. By following protocols of laser treatment, remarkable recoveries from what were thought to be incurable diseases have been achieved.

While the invention has been described with preferred specific embodiments thereof, it will be understood that this description is intended to illustrate and not to limit the scope of the invention, which is defined by the following claims.

I claim:

1. A holistic method of therapeutic laser treatment for body tissues in a problematic area, comprising the following steps:

using a laser discharge probe to target irradiation to the tissues in the problematic area;

using a laser discharge probe to specifically target irradiation to a traditional treatment point, as defined in Eastern medicine, which is positioned along an energy flow path which passes through the problematic area; and, using a laser discharge probe to target irradiation to a less dense concentration of nerve endings than the traditional treatment point, said less dense concentration of nerve endings also being positioned along the energy flow path which passes through the problematic area so that energy flow is normalized in and through the problematic area.

2. A holistic method of laser therapeutic treatment as in claim 1 further comprising the step of additionally treating a site along the energy flow path which is remote from a body portion containing the problematic area and which contains neurologically malfunctioning sensory and motor nerves.

3. A holistic method of laser therapeutic treatment as in claim 1 wherein the energy flow path comprises a meridian of energy flow as defined in acupuncture and wherein the treatment point along the energy flow path comprises an acupuncture point.

4. A holistic method of laser therapeutic treatment as in claim 1 wherein the energy flow path comprises a Jin Shin Jyutsu energy flow path and wherein the treatment point along the energy flow path comprises an energy sphere.

5. A method as in claim 1 further comprising the step of treating a chakra.

6. A holistic method of laser therapeutic treatment as in claim 1 wherein the energy flow path comprises at least one of, a meridian of energy as defined in acupuncture, and a Jin Shin Jyutsu energy flow path; and wherein the treatment point along the energy flow path comprises at least one of, an acupuncture point, and an energy sphere.

7. A method as in claim 6 wherein the treatment point has an area between 0.1 to 5 cm·cm.

8. A holistic method of laser therapeutic treatment as in claim 6 wherein the treatment point may additionally comprise a point along the meridians of energy flow which contains less dense concentrations of nerve endings than an acupuncture point.

9. A method as in claim 7 wherein sites showing vestiges of former injury are targeted to promote healing and reduce inherent impedance to energy flow therethrough.

10. A holistic method of laser therapeutic treatment as in claim 8 wherein the laser discharge probe is dragged along the energy path to facilitate normalization of energy flow therealong.

11. A holistic method of laser therapeutic treatment as in claim 8 wherein a diabetic neuropathy is treated.

12. A holistic method of laser therapeutic treatment as in claim 8 wherein joint injuries are treated.

13. A holistic method of laser therapeutic treatment as in claim 8 for pain felt in a particular problematic body area is treated.

14. A method as in claim 4 wherein the total energy/area applied to each individual site is generally in the range of 18–240 joules/cm·cm, sufficient energy to produce tissue warming, but insufficient energy to thermally damage the tissue.

15. A method as in claim 8 wherein the irradiance rate at the treatment site is in the range of generally 100–1200 mw/cm·cm.

16. A method as in claim 7 wherein treatment along the energy flow path is in a direction of energy flow as defined in Eastern medicine.

17. A method as in claim 16 further comprising the step of evaluating effected changes with Kirlian photography to ensure energy flow has been normalized.

18. A holistic method of laser therapeutic treatment as in claim 16 further comprising the step of using a grounded metal member positioned to facilitate conduction of the energy flow along the energy path thereto.

19. A holistic method of laser therapeutic treatment as in claim 18 wherein the metal member comprises a plate.

\* \* \* \* \*

UNITED STATES PATENT AND TRADEMARK OFFICE
CERTIFICATE OF CORRECTION

PATENT NO. : 6,302,900 B1 Page 1 of 1
DATED : October 16, 2001
INVENTOR(S) : Thomas E. Croley et al.

It is certified that error appears in the above-identified patent and that said Letters Patent is hereby corrected as shown below:

<u>Title page,</u>
Item [76], incorrectly lists all inventors. They should be listed as such at (76):

-- Thomas E. Croley, 3008 Croydon Street, Denton, TX 76209-1300
Jeffrey M. Riggs, 2375 Vantage Drive, Colorado Springs, Colorado 80919;
Thomas R. Radebaugh, 4895 Daybreak Circle, Colorado Springs, Colorado
Fred B. Riggs, Van Kleek Road, Millis, Massachusetts 02054 --

Signed and Sealed this

Eighth Day of April, 2003

JAMES E. ROGAN
*Director of the United States Patent and Trademark Office*